United States Patent [19]

Alburger

[11] 3,930,407

[45] Jan. 6, 1976

[54] WATER-WASHABLE INSPECTION PENETRANT EMPLOYING MINERAL SOLVENT AND A FATTY ACID SOLUBILITY PROMOTER

[76] Inventor: James R. Alburger, 5007 Hillard Ave., La Canada, Calif. 91011

[22] Filed: Jan. 7, 1974

[21] Appl. No.: 431,236

[52] U.S. Cl. .................... 73/104; 73/36; 252/52 R; 252/301.2 P; 252/408
[51] Int. Cl.² ............ G01N 19/08; G01N 31/22; G01N 31/00; C09K 11/00; C09K 3/00
[58] Field of Search ........... 252/408, 301.2 P, 52 R; 73/104, 36

[56] References Cited
UNITED STATES PATENTS

| | | | |
|---|---|---|---|
| 2,478,951 | 8/1949 | Stokely et al. | 252/408 |
| 2,636,127 | 4/1953 | De Forest et al. | 73/104 |
| 2,676,487 | 4/1954 | Clarke | 252/408 |
| 2,806,959 | 9/1957 | De Forest et al. | 252/408 |
| 2,871,697 | 2/1959 | Sockman | 252/408 |
| 3,311,479 | 3/1967 | Alburger | 252/408 |
| 3,415,112 | 12/1968 | Alburger | 252/408 |
| 3,636,759 | 1/1972 | Alburger | 73/104 |
| 3,647,705 | 3/1972 | Mlot-Fijalkowski | 252/301.2 R |

OTHER PUBLICATIONS

"Surface Activity," 2nd Ed. Rev., Moilliet, J., Collie, B., & Black, W., E & F. N. Spon Ltd., London, pp. 251–253 (1961).

*Primary Examiner*—Leland A. Sebastian
*Assistant Examiner*—T. S. Gron

[57] ABSTRACT

Water-washable inspection penetrant compositions which avoid the use of conventional solubilizing detergents. The penetrants comprise an oil vehicle containing a dissolved indicator dye and a fatty acid ingredient dissolved to a concentration within the range of from about 2% to about 25%. The fatty acid ingredient acts as a solubility promoter to permit the penetrant composition to be removed from test surfaces by a spray-wash of water.

4 Claims, No Drawings

WATER-WASHABLE INSPECTION PENETRANT EMPLOYING MINERAL SOLVENT AND A FATTY ACID SOLUBILITY PROMOTER

RELATED PATENT APPLICATION

Application Ser. No. 385,795 — filed Aug. 6, 1973, for WATER-SOLUBLE INSPECTION PENETRANT COMPOSITION EMPLOYING DIMETHYL NAPHTHALENE.

The present invention relates to water-washable inspection penetrant compositions. More particularly, the invention relates to so-called "oil-phase" water-removable penetrants which comprise essentially a liquid vehicle consisting of a water-insoluble oil or mineral solvent, and in which a small but finite degree of water-solubility is imparted to the oil by means of a "solubility promotor" ingredient.

Penetrant inspection processes have been well known in the prior art and have had as their purpose the detection in test bodies of extremely small surface discontinuities and subsurface flaws having surface openings. The test bodies, or parts, may be constructed of metal, ceramic, or other material. The known processes have involved nondestructive inspection penetrant testing procedures, with the usual procedure including, as a first step, the immersion of the test bodies in a penetrant flaw tracer liquid having dissolved therein either a fluorescent dye or a nonfluorescent visible-color dye. The penetrant flaw tracer liquid usually employed has been formulated of an oily liquid vehicle within which vehicle the dye is dissolved.

After immersion of the test bodies in the penetrant for an appropriate dwell period, the test bodies are withdrawn from the liquid and are then subjected to draining, emulsification, and washing operations, for the purpose of removing any penetrant liquid adhering to the surfaces thereof. Minute entrapments of the penetrant liquid, however, remain in any surface discontinuities or subsurface flaws having surface openings, even though extremely small. If the penetrant liquid employed contains a dissolved fluorescent dye, the entrapments may be rendered visible by exposure of the surfaces of the test bodies to ultraviolet radiation. If, on the other hand, the penetrant liquid contains a dissolved nonfluorescent visible-color dye, the entrapments can be viewed in ordinary light.

Two major types of penetrant inspection processes have been utilized. In the case of the so-called "post-emulsifier" type of penetrant inspection process, the penetrant inspection liquid is removed from the surfaces of the test bodies during the washing step through the use of water together with a suitable emulsifier composition. In accordance with the so-called "self-emulsifiable", or water-washable, type of penetrant process, the oily vehicle of the penetrant flaw tracer liquid is compounded together with one or more detergents. As a result, upon contact with water, the penetrant liquid forms an emulsion. Consequently, after the test bodies have been immersed in the penetrant liquid, they may simply be rinsed in water, whereupon the surface penetrant liquid becomes emulsified and is removed without the use of a supplementary emulsifier composition.

The so-called "oil-phase" water-washable penetrants have in the past been comprised essentially of an oily vehicle containing an appropriate concentration of detergent material, sufficient to render the oily mixture emulsifiable in water. I have discovered that the presence of detergent material in the penetrant formulation causes an effect of "adsorption", such that when the penetrant comes in contact with test surfaces which have a substantial amount of fine surface porosity, the penetrant tends to be adsorbed into the large surface area provided by the fine-porosity condition, producing an undesirable amount of background indications.

In connection with the feature of flaw detection performance of a water-washable inspection penetrant, and even post-emulsifier type penetrants and solvent remover type penetrants, I have discovered a hitherto unrecognized performance parameter, and I have reported this discovery in several technical papers presented before the American Society for Nondestructive Testing. Also, requirements pertaining to this performance parameter of "Indication Depletion Time Constant" have been included in applicable Military and Industrial penetrant material specifications.

In essence, I have found that when tested using a standardized craze-cracked panel, each water-washable inspection penetrant exhibits a characteristic rate of depletion of penetrant entrapments upon contact with water remover. Since this depletion follows an exponential curve, it is possible to assign a "depletion time constant" to a given characteristic curve. Although the Indication Depletion Time Constant may be expressed in various ways, present practice is to state a given Indication Depletion Time Constant as the time in seconds of remover contact for the effective magnitude of the standardized entrapment to become diminished to 50% of its initial value.

The parameter of Indication Depletion is important with regard to the flaw detection performance of a given penetrant, since it determines the so-called "stability" of indications in the presence of a remover. Thus, it is important to exercise control over the feature of Indication Depletion Time Constant.

I have discovered that the Indication Depletion Time Constant of a given penetrant composition is roughly an inverse function of the concentration of surfactant (detergent) material which is present. As the surfactant concentration is reduced, the Indication Depletion Time Constant increases in value. Also, as the surfactant concentration is reduced, the water tolerance of the penetrant composition diminishes, water tolerance being the maximum percent of water which may be added to the penetrant composition without cousing clouding or separation of the oil-detergent mixture.

Thus, I have discovered that in designing water-washable penetrants for enhanced values of Indication Depletion Time Constant, it is necessary to reduce the concentration of surfactant in the penetrant composition. I have disclosed this concept in my copending application Ser. No. 385,795, filed Aug. 6, 1973, for "Water-Soluble Inspection Penetrant Composition Employing Dimethyl Naphthalene", and have disclosed various "Formats" of penetrant composition which provide controllable levels of Indication Depletion Time Constant.

In the aforesaid copending application Ser. No. 385,795, I have disclosed oil-detergent mixtures, which I designate "A-Format" penetrants, in which the surfactant content is about 25%, and the water tolerance is about 10%. I have also disclosed compositions which I designate "B-Format" penetrants, in which the surfactant content is about 15%, and the water tolerance is about 5%. Finally, I have disclosed compositions, which I designate "C-Format" penetrants, in which the surfactant content is about 8%, and the water tolerance is about 2%. In these A, B, and C-Format penetrants, the Indication Depletion Time Constant values are progressively increased as the surfactant content is decreased.

In accordance with my concept of controlling Indication Depletion Time Constant values by adjusting the concentration of surfactant, I have theorized that it should be possible to still further increase the Depletion Time Constant values by further reducing the surfactant content, even to zero. However, I have found that when oil-surfactant compositions are formulated wherein the surfactant content is in the range of or less than about 1% to 5%, the solubility of the composition in water diminishes rapidly and approaches zero at zero content of surfactant. Thus, in oil-surfactant mixtues, it does not appear to be practical to reduce the surfactant concentration below a certain critical value in the range of 1%.

Also, and as mentioned above, I have discovered that all liquid dye penetrant compositions exhibit an effect of adsorption with respect to the liquid-solid interface which is present on test parts, such that the penetrant tends to be retained on test surfaces, resisting removal by washing, even though the liquid is readily soluble in water. In many cases, the effect of adsorption is negligable, particularly where the test surface is smooth. But where the test surface is rough, or if a fine-porosity condition exists, as on anodized surfaces, the effective area of the surface which is exposed to contact with the penetrant may become exceedingly large, and any adsorption effects which exist become correspondingly more pronounced.

Adsorption is an interfacial function, and I have found that it is augmented by any surface-active materials, such as detergents, which may be present. I have found that by increasing the detergent (surfactant) content of a penetrant, its water solubility is increased, and the effect of adsorption is also increased.

Thus, in an inspection penetrant having a high concentration of surfactant which is employed on test surfaces which contain cracks in the presence of fine surface porosity, the high content of surfactant renders the penetrant soluble in wash water so that penetrant entrapments in cracks are readily removed, but the penetrant is at the same time strongly adsorbed into the fine surface porosity, producing a condition of severe background indications. The result is that the crack indications may be washed out completely, while the background of fine-porosity indications is not removed. When a condition such as this occurs, it may be said that the penetrant exhibits a poor "signal-to-noise ratio".

According to the above-described behaviour of oil-surfactant type water-washable penetrants, I have theorized that signal-to-noise ratio could be improved by reducing the surfactant content, and could be increased to a maximum by reducing the surfactant content to zero. As explained above, the penetrant becomes inoperable at zero surfactant content due to the fact that the oily composition becomes insoluble in water and will not wash from test parts.

I have discovered that it is possible to employ an oily liquid as the vehicle for a dyed liquid penetrant, and without any surfactant ingredient, and I have found that it is possible to induce sufficient water-solubility in the oily liquid so that it may be washed from test surfaces, yielding a good signal-to-noise ratio.

The principal object of the invention, therefore, is to provide oily penetrant compositions which contain no surfactant material, but which contain a solubility promoter sufficient to induce a small but finite degree of water-solubility to the penetrant composition.

This and other objects of the invention will in part be obvious and will in part become apparent from the following description thereof.

I have found that the addition of from 2% to 25% of a fatty acid to an oily penetrant vehicle will augment the water-solubility of the mixture, such that surface penetrant may be readily removed from test parts under conditions of pressure-spray washing. Also, I have found that the rate of wash removal may be accelerated by increasing the temperature of the wash-water spray, at least up to about 150° F.

In the compositions of the present invention, both of the essential ingredients, oil and fatty acid, are, individually, insoluble in water. However, when combined in the proportions indicated, the mixtures exhibit the unexpected feature of enhanced water-solubility. Also, the effect of adsorption is at a relatively low level in the compositions of the invention, as compared with conventional oil-surfactant type compositions, thereby yielding good signal-to-noise ratios.

For the purpose of the present invention, the mineral solvent ingredient of the compositions is defined as a light mineral oil such as kerosene, diesel fuel, absorption oil, or a light lubricating oil such as white oil, or the so-called Pacific Base Oil. The oils may be aromatic in character, and light aromatic solvents such as xylene, benzene, toluene, or dimethyl naphthalene may be utilized. Insofar as the various mineral oils and solvents are concerned, viscosity may range from a few centistokes up to as much as several hundred centistokes, and the aniline point may fall anywhere within the range of from above 200° F. down to quite low values of mixed aniline point, such as the value of 53° F., which is characteristic of dimethyl naphthalene.

I have found that virtually any mineral solvent or mineral oil may be employed as the mineral solvent ingredient of the compositions of the invention. However, low viscosity oils are preferred, as are oils or solvents having flash points above 200° F. Thus, a preferred type of mineral oil is that which is represented by the class of "Base Oils", as produced by Standard Oil Co. (Chevron). These oils may be either naphthenic or paraffinic, depending on the crude stocks from which they are derived.

Aniline point of the oil ingredient is not critical, however it is preferred that the aniline point shall be below about 130° F. in order to provide good solubility for the indicator dye or dyes which may be employed. Any one of a large number of commercially available mineral solvents may be selected which have aniline points low enough to provide good solubility for the indicator dye. If a "base oil 50 pale" is used, its aniline point may fall in the range of from 180° F. to 200° F. The addition of a highly aromatic solvent, such as dimethyl naphthalene, will reduce the aniline point to any desired value, down to a mixed aniline point of about 53° F., which is the characteristic aniline point of pure dimethyl naphthalene.

For example, a mixture of equal parts of dimethyl naphthalene and Base Oil 50 Pale will provide adequate solvency for the high concentrations of fluorescent dye, up to as much as 30%, which may be required for certain high-sensitivity usage. Where dye concentrations are less, down to 0.2% in some cases, the aromatic content of the oil vehicle need not be so great. In any event, the aniline point of the oil mixture should be below about 150° F., at least for best results. Dye concentrations may be selected in accordance with known practices for establishing dye performance sensitivity values of penetrants.

The fatty acid ingredient of the compositions of the invention may be any one or a combination of fatty acids, including:
  Oleic acid
  Soya Alkyd acid (linoleic)
  Coconut fatty acid (lauric)
  Palmitic acid
  Tall Oil fatty acid
  Naphthenic acid.

In the above listing, naphthenic acid is indicated as being a "fatty acid". Although naphthenic acid is not normally classified as a fatty acid, I include it in that category and define it as such for the purposes of this invention.

Most of the useful fatty acids are normally liquid at room temperature, however many fatty acids which are solid or semi-solid at room temperature may be utilized as solubility promotors in accordance with the invention, so long as they dissolve in the mineral oil constituent. For example, Palmitic acid is a flaky solid at room temperature, while Coconut fatty acid is a pasty solid at room temperature. These, and similar fatty acids dissolve readily in the oil mixture used as the base vehicle of the penetrants of the invention, and they act as solubility promoters in the same way as liquid fatty acids.

EXAMPLE

A family of D-Format fluorescent penetrants was prepared as follows: A mineral solvent mixture was first prepared by mixing equal parts of dimethyl naphthalene and Chevron (T.M.) Base Oil 50 Pale. This mixture was found to have an aniline point in the range of 110° F. to 115° F. Using this mineral solvent mixture, a family of penetrant vehicles was prepared as follows:

| | |
|---|---|
| Mineral solvent mixture | 98% to 75% |
| Oleic acid | 2% to 25% |

A fluorescent indicator dye was added to the thus-prepared penetrant vehicle using various concentrations ranging from 0.2% up to 30% by weight.

Within the bounds of the foregoing formulations, it was found that the optimum and preferred content of oleic acid is about 7%, the preferred indicator dye is the fluorescent dye 4-methyl-7-diethylamino coumarin, and its concentration may range from 0.3% to 10% or more. In addition to the coumarin "sensitizer" dye, it was found that a small amount of green-yellow color-former dye may be added to the penetrant in accordance with known methods, to a concentration of about 0.1% to 0.6%, with a preferred concentration of about 0.4%. This color-former dye provides a shift in the fluorescent color from blue to green, whereby seeability of flaw indications is improved. Any one or a combination of a wide variety of visible-color or fluorescent dyes may be employed in accordance with known practices.

The water-washable penetrants of the invention may be employed in accordance with known use techniques, except that consideration must be given to the fact that they dissolve slowly in water and a certain amount of agitation or spray action of the wash water is required in order to provide effective removal of surface penetrant. The effectiveness of wash-removal may be enhanced by heating the wash water to a temperature of up to 150° F., a preferred temperature of the wash water being about 140° F.

In the example given above, substitutions may be made of any of the fatty acids which have been disclosed, and with equivalent results. Also, substitutions may be made of any of the oil and solvent materials which have been disclosed, also with equivalent results.

The penetrant compositions of the invention not only dissolve slowly in water, but their solubility in water is quite low. Hence, as penetrant is removed from test surfaces, most of the penetrant tends to float to the surface of the wash water and may be recovered and re-used. The small amount of penetrant which dissolves in the water may be extracted by a process such as that which is disclosed in my copending application Ser. No. 432,752, filed Jan. 11, 1974 for "A Closed-Loop Water-Washable Inspection Penetrant Process". Penetrant which is thus extracted may be re-used, and the purified wash water may be re-used.

The penetrant compositions of the invention differ from conventional oil-detergent type water-washable penetrants in that they do not form highly stable emulsions in wash water. Oil-detergent type penetrants cannot be readily separated from wash water, due to their tendency to form stable emulsions, and they are, therefore, not adaptable to closed-loop operation as are the penetrants of the present invention.

It will be understood that I have devised a new and novel class of water-removable inspection penetrants. Although the invention has been describe with reference to particular embodiments thereof, it will be understood that various changes may be made therein without departing from the spirit of the invention or the scope of the appended claim.

I claim:

1. In a water-washable inspection penetrant process in which a water-dispersible dyed liquid penetrant is applied to test parts, surface penetrant is removed by washing said test parts with water, and said parts are inspected for residual entrapments of penetrant liquid in surface flaws, the improvement wherein said water-washable penetrant consists essentially of the following formulation, stated in weight percentages:

| | |
|---|---|
| Mineral solvent | 98% to 75% |
| Fatty acid | 2% to 25% | said penetrant vehicle having dissolved therein an indicator dye to a concentration within the range of from about 0.2% up to about 30%.

2. A process in accordance with claim 1 in which said fatty acid is at least one member selected from the group consisting of:
  Oleic acid,
  Soya Alkyd acid,
  Coconut fatty acid,
  Palmitic acid,
  Tall Oil fatty acid, and
  Naphthenic acid.

3. A process in accordance with claim 1 in which said fatty acid is Oleic acid.

4. A process in accordance with claim 1 in which said mineral solvent is a mixture of mineral oils having an aniline point within the range of from about 200° F. down to a mixed aniline point of about 53° F.

* * * * *